(12) United States Patent
Furihata et al.

(10) Patent No.: US 9,150,817 B2
(45) Date of Patent: Oct. 6, 2015

(54) PROCESS FOR PREPARING CONCENTRATED POLYUNSATURATED FATTY ACID OIL

(75) Inventors: Kiyomi Furihata, Tokyo (JP); Hiroyuki Kawahara, Tokyo (JP); Nobushige Doisaki, Tokyo (JP)

(73) Assignee: Nippon Suisan Kaisha, Ltd., Chiyoda-Ku, Tokyo (JP)

( * ) Notice: Subject to any disclaimer, the term of this patent is extended or adjusted under 35 U.S.C. 154(b) by 375 days.

(21) Appl. No.: 12/296,786

(22) PCT Filed: Apr. 13, 2007

(86) PCT No.: PCT/JP2007/058134
§ 371 (c)(1),
(2), (4) Date: Oct. 10, 2008

(87) PCT Pub. No.: WO2007/119811
PCT Pub. Date: Oct. 25, 2007

(65) Prior Publication Data
US 2009/0176284 A1  Jul. 9, 2009

(30) Foreign Application Priority Data
Apr. 13, 2006 (JP) ................................. 2006-111039

(51) Int. Cl.
| | | |
|---|---|---|
| C11C 1/00 | (2006.01) |
| C12P 7/64 | (2006.01) |
| C12P 7/62 | (2006.01) |
| C07K 14/00 | (2006.01) |
| C11C 3/00 | (2006.01) |
| C11C 3/04 | (2006.01) |
| C07K 14/195 | (2006.01) |
| C07K 14/21 | (2006.01) |

(52) U.S. Cl.
CPC .............. *C11C 3/003* (2013.01); *C12P 7/6472* (2013.01); *C07K 14/195* (2013.01); *C07K 14/21* (2013.01); *C11C 3/00* (2013.01); *C11C 3/04* (2013.01); *C12P 7/64* (2013.01); *C12P 7/6427* (2013.01); *C12P 7/6436* (2013.01); *C12P 7/6445* (2013.01); *C12P 7/6454* (2013.01)

(58) Field of Classification Search
CPC .............. C11C 3/00; C11C 3/04; C12P 7/64; C12P 7/6427; C12P 7/6436; C12P 7/6445; C12P 7/6454; C07K 14/195; C07K 14/21

USPC ................... 435/134, 135, 271; 530/350
See application file for complete search history.

(56) References Cited

U.S. PATENT DOCUMENTS

| | | | | |
|---|---|---|---|---|
| 3,274,159 A | * | 9/1966 | Kluiber | .......................... 528/289 |
| 5,935,828 A | | 8/1999 | Zaks et al. | |
| 5,945,318 A | | 8/1999 | Breivik et al. | |
| 5,968,792 A | * | 10/1999 | Wenzel et al. | ................. 435/134 |
| 7,935,508 B2 | | 5/2011 | Schörken et al. | |

FOREIGN PATENT DOCUMENTS

| | | |
|---|---|---|
| JP | 58-165796 | 9/1983 |
| JP | 59-14793 | 1/1984 |
| JP | 63-287492 | 11/1988 |
| JP | 3-108489 | 5/1991 |
| JP | 2004-222595 | 8/2004 |
| WO | 90/13656 | 11/1990 |
| WO | 95/24459 | 9/1995 |
| WO | WO9827219 A1 | 6/1998 |
| WO | WO2006077022 A3 | 7/2007 |

OTHER PUBLICATIONS

Rakshit et al., 2000, Bioprocess Engineering, vol. 23, p. 251-255.*
Li et al., 1993, Journal of American Oil Chemists' Society, vol. 70, No. 8, p. 745-748.*
Msika et al., 2003, US 20030129268 A1.*
Li et al., 1993, Enzyme Microb. Technol., vol. 15, p. 601-606.*
Dordick, "Enzymatic catalysis in monophasic organic solvents", Enzyme Microb. Technol., vol. 11, Apr. 1989, pp. 194-211.
Hata et al., "Separation Technology of EPA and DHA", Bunri Gijutsu, 2000, 30(6), 9 pages, with translation.
Zui et al., "Lipase-catalyzed alcoholysis to concentrate the n-3 polyunsaturated fatty acids of cod liver oil", Enzyme Microb. Technol., vol. 15, Jul. 1993, pp. 601-606.
Supplementary European Search Report, European Application No. EP07741570 dated Dec. 7, 2012, 8 pages.

* cited by examiner

*Primary Examiner* — Shin Lin Chen
(74) *Attorney, Agent, or Firm* — Fish & Richardson P.C.

(57) ABSTRACT

The present invention provides a process for concentrated PUFA oil, characterized in that alcoholysis reaction using lipase is carried out in the presence of a small amount of water and at least one compound as an additive selected from magnesium oxide, magnesium hydroxide, calcium oxide and calcium hydroxide, and then separation is conducted to obtain a glyceride fraction.

10 Claims, No Drawings

PROCESS FOR PREPARING CONCENTRATED POLYUNSATURATED FATTY ACID OIL

TECHNICAL FIELD

The invention relates to a process for preparing oil and fat containing polyunsaturated fatty acid (referred to as "PUFA" hereinafter) in high concentration by alcoholysis using lipase.

BACKGROUND ART

Eicosapentaenoic acid (referred to as "EPA" hereinafter) and docosahexaenoic acid (referred to as "DHA" hereinafter), which are categorized as n-3 polyunsaturated fatty acids, have a variety of biological effects, and are used as medical products, health food products, food product materials, and the like. EPA ethyl ester is used as a therapeutic agent for treating arteriosclerosis and hyperlipidemia. Further, beverages to which fish oil containing EPA and DHA has been added have been approved as a food for specified health uses. Furthermore, demand for these fatty acids as a supplement is very high in Japan and other countries.

Since PUFAs have many double bonds, they are very unstable to oxidation. Therefore, in a process for preparing PUFA-containing oil and fat, it is very desirable to use an enzyme reaction that proceeds under mild conditions, such as at room temperature and normal pressure.

It has been known that some of lipase products for industrial use, which are obtained mainly from microorganisms, have a property of less reacting with PUFAs. PUFA-concentrated oil and fat can be produced by dominantly liberating shorter-chain fatty acids using lipase having such a property, followed by removal of the free fatty acids. For instance, a process for preparing DHA-concentrated oil and fat by hydrolysis of tuna oil using a lipase derived from *Candida cylindracea* followed by removal of the free fatty acids has been reported (Patent Document 1).

It has been known that for enzyme reactions even in an organic solvent, water plays an important role on enzyme activation (non-Patent Document 1). It has been reported that when PUFAs are concentrated from cod liver oil by alcoholysis, which is a reaction to eliminate fatty acids from glycerides by treating with alcohol, and addition of water promotes the lipase reaction (Non-Patent Document 2). On the other hand, it has been reported that such an alcoholysis reaction of oil and fat proceeds under virtually anhydrous conditions with certain lipases (Patent Document 2). Nevertheless, the amount of lipase used was very high at 10% relative to the amount of oil, and the lipase must be immobilized to improve productivity.

Alcoholysis reaction carried out with lower alcohols yields fatty acid lower alcohol ester, which can be easily removed by distillation or the like.
[Patent Document 1] JP 58-165796 A
[Patent Document 2] JP 9-510091 A
[Non-Patent Document 1] J. S. Dordick, "Enzymatic catalysis in monophasic organic solvents", *Enzyme Microb. Technol.*, 1989, 11, April, 194-211.
[Non-Patent Document 2] L. Zui and O. P Ward, "Lipase-catalyzed alcoholysis to concentrate the n-3 polyunsaturated fatty acids of cod liver oil", *Enzyme Microb. Technol.*, 1993, 15, Jul., 601-606.

DISCLOSURE OF THE INVENTION

Problems to be Solved by the Invention

Although concentrated oil prepared by concentrating PUFAs from fish oil and the like, using such a property of lipases, has already been available on the market, there are limits to the degree of concentration, and it is difficult to obtain a highly concentrated product without using a large amount of enzyme. Further, it is necessary to repeatedly conduct operations of reaction, removal of unwanted components and the like, and the resulting product has to be very expensive due to the high cost of production. An object of the present invention is to provide a method for concentrating PUFAs, in particular EPA, DHA and the like, contained in starting oil.

Means for Solving the Problems

As a result of conducting comprehensive research into reactions using industrial lipases, the inventors have established that even when an amount of lipase used is small, efficiency of alcoholysis reaction is significantly enhanced by addition of a small amount of magnesium oxide (referred to as "MgO" hereinafter), magnesium hydroxide, calcium oxide, calcium hydroxide or the like. Further, it has been found that the property of certain lipases, which less react with the target product (i.e. PUFAs such as EPA, DHA and the like), is strictly maintained in the reaction.

The summary of the invention relates to a process for preparing PUFAs-concentrated oil, which comprises subjecting fat and oil containing PUFAs to alcoholysis reaction using lipase in the presence of a small amount of water and at least one compound selected from magnesium oxide, magnesium hydroxide, calcium oxide and calcium hydroxide, followed by separation to obtain glyceride fraction.

Thus, according to the present invention, there is provided a process for preparing polyunsaturated fatty acids-concentrated oil, comprising: a step to subject fat and oil containing polyunsaturated fatty acids as a fatty acid composing the fat and oil to alcoholysis reaction using lipase in the presence of a small amount of water and at least one compound selected from magnesium oxide, magnesium hydroxide, calcium oxide and calcium hydroxide; and a step to separate glyceride fraction for obtaining fatty acids composing the oil and fat.

Advantages of the Invention

The present invention enhances reactivity of the enzyme by addition of inexpensive additives and a small amount of water, and also enhances selectivity of the enzyme so as to react less with PUFAs linking to glyceride via a ester bond. As a result, concentrated oil highly containing PUFAs can be prepared at high yield and low cost.

EMBODIMENTS OF THE INVENTION

In the present invention, a polyunsaturated fatty acid (PUFA) refers to a fatty acid having 16 or more carbon atoms and two or more double bonds. Well known examples thereof include eicosapentaenoic acid (EPA), docosahexaenoic acid (DHA), arachidonic acid, linolenic acid, linoleic acid and the like. In the present invention, oil and fat containing polyunsaturated fatty acid are, but not limited particularly, are oil containing a polyunsaturated fatty acid as a fatty acid composing the oil and fat. Examples thereof include marine product oil such as fish oil, microorganism oil, alga oil, vegetable oil and the like, each of which contains a polyunsaturated fatty acid. As the starting material of the present invention, the oil and fat may be used as crude oil (expressed oil), or as oil subjected to any purification process. In the process of the present application, water content is a key factor, and it is preferable to confirm water content of oil and fat. The process of the present application is suitably applied to concentration of a fatty acid having 20 or more carbon atoms and 4 to 6 double bonds, in particular 20 to 22 carbon atoms and 4 to 6 double bonds among polyunsaturated fatty acids. Examples of the fatty acid suitable for the process of the present invention include EPA, DHA, arachidonic acid, and docosapentaenoic acid.

The term "oil and fat" mainly refers to triglycerides of fatty acids, but in the present invention the term also refers to glyceride including diglyceride, monoglyceride.

In the present invention, "concentration of polyunsaturated fatty acid" refers to increasing a value of (amount of polyunsaturated fatty acid)/(total amount of fatty acids) after a reaction, relative to that of the oil and fat used as a starting material. Namely, oil and fat having a larger value of (amount of polyunsaturated fatty acid)/(total amount of fatty acids) than that of starting oil and fat corresponds to "polyunsaturated fatty acid-concentrated oil".

In the present invention, "glyceride" is a generic term for triglyceride, diglyceride and monoglyceride of fatty acids.

The lipase used in the present invention is not limited particularly, but it catalyses alcoholysis reaction and has a property of less reacting with a PUFA. Examples of the lipase include lipases derived from microorganisms of *Alcaligenes* sp., such as Lipase QLM, Lipase QLC and Lipase PL (manufactured by Meito Sangyo Co., Ltd.); lipases derived from microorganisms of *Burkholderia cepacia*, such as Lipase PS (manufactured by Amano Enzyme Inc.); lipases derived from microorganisms of *Pseudomonas fluorescens*, such as Lipase AK (manufactured by Amano Enzyme Inc.); lipases derived from microorganisms of *Thermomyces lanuginosa*, such as Lipase TL IM (manufactured by Novozymes) and the like. An amount of a lipase used is not limited particularly. However, a lipase in powder form is preferably used in 10 units/g or more relative to oil and fat, and in particular for practical use, it is preferably used in 30 units/g or more relative to oil and fat in light of a reaction rate. An immobilized lipase is preferably used in 0.01 (w/w) or more relative to oil and fat.

MgO, magnesium hydroxide, calcium oxide, or calcium hydroxide may be used as a reaction additive. MgO is preferred, since it provides a high effect and can be used in food products. An additive in powder form, fine particles, granules or the like is preferred in handling thereof, and an additive commercially available for industrial use can be used. An amount of a reaction additive is not limited particularly. However, it is preferably used in a range from 0.01% (w/w) to 30% (w/w), more preferably used in a range from 0.05% (w/w) to 5% (w/w) relative to oil and fat. In addition, it is highly beneficial to add a small amount of water. Water is preferably added in a range from 1% (v/v) to 30% (v/v), more preferably added in a range from 5% (v/v) to 20% (v/v) relative to alcohol used. An alcohol used in the reaction is not limited particularly. However, ethanol is one of the most preferred alcohols. An amount of alcohol is in a range from 0.2 to 5 equivalents, more preferably in a range from 0.2 to 1.5 equivalents, relative to fatty acids.

A method for the reaction is not limited, but requires mixing a certain amount of starting oil and fat, water, a reaction additive and alcohol. Generally, the reaction is conducted by stirring the mixture effectively at a temperature in which enzyme exhibits high activity (e.g. 20° C. to 60° C.) for a reaction time from about 1 to 24 hours. An enzyme immobilized in a column may be used for conducting the reaction. After the reaction, a reaction additive, enzyme and the like can be removed by filtration, washing with aqueous solution and the like, and then isolation and purification of glyceride give PUFA-concentrated oil as a glyceride fraction. A method for separation of glyceride fraction is not limited particularly. However, an isolation method using distillation such as molecular distillation, short path distillation, or various chromatographies and the like can be used therefor. Purification may be conducted by a method generally used for purification of oil and fat, such as various chromatographies, steam distillation, and the like.

The present invention is illustrated specifically with the following examples, but the present invention is in no way limited by these examples. It should be noted that the PUFA content of the starting oil and glyceride fraction was determined from the area ratio of gas chromatography conducted after conversion of the resulting product to methyl ester. Moreover, the conversion to methyl ester prior to gas chromatography analysis was conducted in accordance with the standard oil and fat testing method specified by the Japan Oil Chemists' Society (Japan Oil Chemists' Society Standard Methods for the Analysis of Fats, Oils and Related Materials (I), 1996, 2.4.1 Fatty acid Derivation Methods: 2.4.1.2-1996 Methyl esterification methods (boron trifluoride-methanol method)).

Example 1

Lipase QLM (*Alcaligenes* sp., Meito Sangyo Co., Ltd; 1.65 mg, 100 units/g), water (17 µL), MgO (Junsei Chemical Co., Ltd., special grade reagent, purity of 99% or higher; 0.25% (w/w) or 2.5% (w/w) relative to oil), and ethanol (170 µL, 0.75 equivalents relative to fatty acids) were added to purified sardine oil (1 g; 28.2% of EPA, 12.5% of DHA, Nippon Suisan Kaisha, Ltd.), and the mixture was stirred for 16 hours at 40° C. After the reaction, the solid content was filtered off and the filtrate was extracted with hexane. The glyceride fraction was separated by preparative TLC using the following procedure (unless otherwise specified, preparative TLC referred to hereinafter was conducted by the same procedure). The extract solution in hexane (150 µL) was applied to preparative TLC plate (silica gel 60F 254 plate, manufactured by Merck), and developed with a mixture of hexane:diethyl ether:acetic acid=70:30:1 (volume rate). After development, the fraction other than ethyl ester fraction was collected as glyceride fraction.

The resulting glyceride fraction was converted to methyl ester and the fatty acid composition was analyzed by gas chromatography. The condition for gas chromatography analysis is indicated as follows:
Capillary Column: DB-WAX (J&W Scientific), Fused Silica Capillary Column, 0.25 mm I.D.×30 m, 0.25 µm film thickness;
Carrier gas: helium;
Detector: 250° C., FID;
Inlet: 250° C., split rate=100:1
Column Temp.: 180° C. to 3° C./min, then to 230° C. (15 min)
Apparatus: Hewlett Packard 6890

Lipase PS (3.3 mg, 100 units/g, *Burkholderia cepacia*, Amano Enzymes) was also reacted under the same conditions.

As comparative examples, ethanolysis reaction each with the lipases was carried out under the same conditions with the exception that no water or MgO was added, only water was added, or only MgO was added at 0.25% (w/w).

The lipid composition of the glyceride fraction was analyzed using TLC/FID (Yatroscan TH-10, Mitsubishi Kagaku Yatron Corporation) by spotting a 5 wt % hexane solution (1 µL) on a silica gel rod and then developing the rod using a mixture of hexane:diethyl ether:acetic acid (90:10:1, volume ratio). The peak area ratios of the glyceride and the ester were obtained from the resulting charts, and the glyceride yield was calculated based on these ratios. The yield of PUFA such as EPA and DHA was calculated from (the PUFA ratio (%) of the glyceride after reaction×the glyceride content (%))/(the PUFA ratio (t) before the reaction). Table 1 shows the results of areas (%) of the EPA and DHA: fatty acid yield regarding the EPA and DHA; and glyceride yield. Table 2 shows the results of the comparative examples.

For example, in Patent Document 2 (JP 9-510091 A), an enzyme in powder form was used at 10% relative to oil, while in the process of the present invention, the amount each of lipases used is 100 units/g (relative to oil, Lipase QLM is 0.165% and Lipase PS is 0.33%). Namely, the result shows that significantly a smaller amount used of the lipase is required to proceed the reaction. Further, the comparative examples clearly indicates the effects of addition of water and MgO on concentration of EPA and the like, in spite of using the same amount of the lipase. The result also shows that increase of addition of MgO resulted in enhancing concentration of EPA. Further, high yield of EPA indicates that the selectivity of the fatty acids in the reaction is maintained.

Example 3

Lipozyme TL IM (*Thermomyces lanuginosus*, Novozymes; 2 mg, 0.1% (w/w) relative to oil), water (34 µL), MgO (0.25% (w/w) or 2.5% (w/w)), and ethanol (340 µL) were added to purified tuna oil (2 g, 6.75% of EPA, 24.3% of DHA, Nippon Suisan Kaisha, Ltd.), and the mixture was stirred for 16 hours at 40° C. As comparative examples, ethanolysis reaction was carried out under the same conditions with the exception that no water or MgO was added, only water was added, or MgO (0.25% (w/w)) only was added. After the reaction, the solid content was filtered off, the glyceride fraction was separated by preparative TLC, conversion thereof to methyl ester was conducted, and the fatty acid composition was analyzed. Table 4 shows the yields of EPA and DHA and glyceride, and Table 5 shows the EPA and DHA area %, fatty acid yield, and glyceride yield of the comparative examples.

The results show that the addition of water and MgO significantly enhanced the concentration of DHA. The concentration of DHA increased as addition amount of MgO

TABLE 1

|  | Starting purified sardine oil | Lipase QLM 0.25% MgO + water | Lipase QLM 2.5% MgO + water | Lipase PS 0.25% MgO + water | Lipase PS 2.5% MgO + water |
| --- | --- | --- | --- | --- | --- |
| EPA area % | 28.8 | 50.6 | 61.5 | 52.2 | 59.7 |
| DHA area % | 12.5 | 16.3 | 16.2 | 15.6 | 17.9 |
| EPA yield (%) |  | 98.5 | 97.5 | 93.2 | 91.7 |
| DHA yield (%) |  | 90.4 | 91.7 | 83.6 | 70.2 |
| Glyceride yield (%) |  | 67.8 | 50.6 | 60.5 | 49.1 |

TABLE 2

|  | Lipase QLM | Lipase QLM + water | Lipase QLM + MgO | Lipase PS | Lipase PS + water | Lipase PS + MgO |
| --- | --- | --- | --- | --- | --- | --- |
| EPA area % | 36.1 | 43.0 | 41.7 | 30.7 | 45.0 | 30.1 |
| DHA area % | 15.2 | 17.5 | 16.4 | 12.9 | 17.1 | 12.3 |
| EPA yield (%) | 99.5 | 94.8 | 98.5 | 99.6 | 85.9 | 99.6 |
| DHA yield (%) | 99.2 | 89.0 | 90.0 | 98.6 | 75.2 | 97.5 |
| Glyceride yield (%) | 83.4 | 74.6 | 69.8 | 96.2 | 55.0 | 98.0 |

Example 2

Using as the starting material sardine oil (15.7% EPA, 8.99% DHA, Nippon Suisan Kaisha, Ltd.) having lower EPA and DHA contents than the sardine oil used in Example 1, ethanolysis reaction was carried out for 16 hours at 40° C. under the same conditions as described in Example 1 using Lipase QLM (1.65 mg, 100 units/g), water (17 µL), MgO (2.5% (w/w)), and ethanol (170 µL), relative to 1 g of oil and fat. Table 3 shows the results of area % and yield of EPA and DHA, and glyceride yield.

TABLE 3

|  | Lipase QLM 2.5% MgO + water |
| --- | --- |
| EPA area % | 43.5 |
| DHA area % | 17.3 |
| EPA yield (%) | 95.5 |
| DHA yield (%) | 80.5 |
| Glyceride yield (%) | 41.9 | increased. Even though the same amount of enzyme was used in the comparative example, the DHA was hardly concentrated.

TABLE 4

|  | Purified tuna oil | Lipozyme TL IM 0.25% MgO + water | Lipozyme TL IM 2.5% MgO + water |
| --- | --- | --- | --- |
| EPA area % | 6.8 | 9.4 | 8.4 |
| DHA area % | 24.3 | 48.2 | 68.7 |
| EPA yield (%) |  | 69.6 | 37.0 |
| DHA yield (%) |  | 99.1 | 83.5 |
| Glyceride yield (%) |  | 50.0 | 29.6 |

TABLE 5

|  | Lipozyme TL IM | Lipozyme TL IM + water | Lipozyme TL IM + MgO |
| --- | --- | --- | --- |
| EPA area % | 7.2 | 7.2 | 7.1 |
| DHA area % | 26.2 | 26.5 | 25.5 |

TABLE 5-continued

|  | Lipozyme TL IM | Lipozyme TL IM + water | Lipozyme TL IM + MgO |
|---|---|---|---|
| EPA yield (%) | 99.2 | 99.0 | 99.5 |
| DHA yield (%) | 99.6 | 99.8 | 99.5 |
| Glyceride yield (%) | 97.2 | 93.5 | 98.0 |

Example 4

To investigate the effects of reaction additives other than MgO, nine reaction additives were used at 1% (w/w) relative to starting oil and the mixture was treated under the same reaction conditions as described in Example 1. That is, Lipase QLM (*Alcaligenes* sp., Meito Sangyo Co., Ltd; 1.65 mg, 100 units/g), water (17 µL), one of the nine reaction additives shown in Table 6 at 1% (w/w) relative to oil, and ethanol (170 µL, 0.75 equivalents relative to fatty acids) were added to purified sardine oil (1 g, 28.2% of EPA, 12.5% of DHA, Nippon Suisan Kaisha, Ltd.), and the mixture was stirred for 16 hours at 40° C. After the reaction was completed, the solid content was filtered off, the glyceride fraction was separated by preparative TLC, conversion thereof to methyl ester was conducted, and the fatty acid composition was determined. Table 6 shows the EPA area % of the glyceride fraction. The result shows that in addition to MgO, magnesium hydroxide, magnesium oxide, calcium oxide, and calcium hydroxide have an effect accelerating EPA-concentration.

TABLE 6

|  | EPA area % | Manufacturer | Grade | Purity min % |
|---|---|---|---|---|
| Magnesium oxide | 56.3 | Junsei Chemical Co., Ltd. | Special grade | 99 |
| Magnesium hydroxide | 54.5 | Wako Pure Chemical Industries, Ltd. | First grade | 97 |
| Magnesium carbonate (basic) | 44.7 | Nacalai Tesque, Inc. | Special grade | $MgCO_3$ 60 to 55% MgO 40 to 45% |
| Magnesium chloride | 30.7 | Wako Pure Chemical Industries, Ltd. | Special grade | 98 |
| Calcium oxide | 46.9 | Wako Pure Chemical Industries, Ltd. | Special grade | 99.9 |
| Calcium hydroxide | 46.6 | Nacalai Tesque Inc. | Special grade | 95 |
| Calcium chloride | 29.6 | Nacalai Tesque Inc. | Special grade | 98.5 |
| Calcium nitrate | 30.1 | Nacalai Tesque Inc. | Special grade | 99.5 |
| Sodium carbonate | 29.9 | Wako Pure Chemical Industries, Ltd. | Special grade | 99.5 |
| Potassium hydrogen carbonate | 36.2 | Nacalai Tesque, Inc. | Special grade | 99.7 |

Example 5

Production of EPA-Concentrated Oil and Fat with Lipase QLM

Lipase QLM (0.83 g, *Alcaligenes* sp, Meito Sangyo Co., Ltd.), water (17 g), MgO (2.5 g), and ethanol (173 mL) were added to purified sardine oil (1 kg, 28.2% of EPA, 12.5% of DHA, Nippon Suisan Kaisha, Ltd.), and the mixture was stirred for 16 hours at 40° C. After centrifugation, the solid content was removed, and the ethanol was distilled off to yield 1.06 kg of oil. The product was washed with dilute sulfuric acid and warm water, and esters and fatty acids were distilled by a thin layer distillation device to yield EPA-concentrated oil (583 g) as a glyceride fraction. Measurement of the fatty acid composition shows 48.3% of EPA and 17.3% of DHA.

Example 6

Production of DHA-Concentrated Oil and Fat with Lipozyme TL IM

Lipozyme TL IM (1 g, *Thermomyces*, Novozymes), water (17 g) MgO (5 g), and ethanol (173 mL) were added to purified tuna oil (1 kg, 6.75% of EPA and 24.3% of DHA) and the mixture was stirred for 16 hours at 40° C. After the solid content was filtered off, ethanol was distilled off to yield 1.07 kg of oil. After washing with phosphoric acid and warm water, esters and fatty acids were distilled by a molecular distillation device to yield DHA-concentrated oil (416 g) as a glyceride fraction. Measurement of the fatty acid composition shows 9.4% of EPA and 52.8% of DHA.

Example 7

Study of the Amount of MgO Added

Alcoholysis was carried out under the same conditions as described in Example 1, that is, Lipase QLM (1.65 mg, 100 units/g), water (17 µL), MgO (0 to 10% (w/w) relative to oil), and ethanol (170 µL, 0.75 equivalent relative to fatty acids) were added to purified sardine oil (1 g, 28.2% of EPA and 12.5% of DHA, Nippon Suisan Kaisha, Ltd.) and the mixture was stirred for 16 hours at 40° C.

The results are shown in Table 7. Increase of addition of MgO accelerated the reaction and the concentration of EPA.

TABLE 7

| Amount of MgO added | EPA area % | DHA area % |
|---|---|---|
| 0 | 43.6 | 17.1 |
| 0.05% | 46.7 | 16.1 |
| 0.1% | 47.2 | 16.2 |
| 0.25% | 50.6 | 16.3 |
| 1% | 56.3 | 17.0 |
| 2.5% | 61.5 | 16.2 |
| 5% | 66.8 | 15.1 |
| 10% | 67.6 | 15.4 |

Example 8

Study of the Amount of Water Added

Lipase QLM (0.83 mg, 50 units/g), water (3.5% to 20% (v/v) relative to ethanol), MgO (0.25% (w/w) relative to oil), and ethanol (170 µL, 0.75 equivalents relative to fatty acids)

were added to purified sardine oil (1 g, 28.2% of EPA, 12.5% of DHA, Nippon Suisan Kaisha, Ltd.) and alcoholysis was carried out by stirring for 16 hours at 40° C.

The results are shown in Table 8. The results indicate that the addition amount of water is preferred to be 5% to 20% (v/v) relative to the amount of ethanol.

TABLE 8

|  | Water (% (v/v) relative to ethanol) | | | | | |
| --- | --- | --- | --- | --- | --- | --- |
|  | 3.5 | 5.8 | 10 | 13 | 16 | 20 |
| EPA area % | 39.3 | 43 | 46.3 | 47.4 | 46.6 | 34.6 |
| DHA area % | 16.3 | 16.7 | 17.0 | 17.5 | 17.7 | 14.7 |

Example 9

Study of the Amount of Ethanol Added

Lipase QLM (0.83 mg, 50 units/g), water (17 μL), MgO (0.25% (w/w) relative to oil), and ethanol (0.5 to 1.5 equivalents relative to fatty acids) were added to purified sardine oil (1 g, 28.2% of EPA, 12.5% of DHA, Nippon Suisan Kaisha, Ltd.) and alcoholysis was carried out by stirring for 16 hours at 40° C.

The results are shown in Table 9. The results indicate that the preferred amount of ethanol is 0.5 to 1.5 equivalents relative to fatty acids.

TABLE 9

|  | Ethanol (equivalents relative to fatty acids) | | | | |
| --- | --- | --- | --- | --- | --- |
|  | 0.5 | 0.67 | 0.75 | 1 | 1.5 |
| EPA area % | 43.1 | 46.38 | 46.3 | 46.5 | 40.2 |
| DHA area % | 16.7 | 15.77 | 17.0 | 17.4 | 16.3 |

Example 10

Study of the Amount of Lipase Used

Lipase QLM (10 to 50 units/g), water (17 μL), MgO (0.25 to 1% (w/w) relative to oil), and ethanol (0.75 equivalents relative to fatty acids) were added to purified sardine oil (1 g, 28.2% of EPA, 12.5% of DHA, Nippon Suisan Kaisha, Ltd.), and alcoholysis was carried out by stirring for 16 hours at 40° C.

The results are shown in Table 10. The results indicate that the preferred amount of lipase is 25 units/g or more. Moreover, it was confirmed that, even with the same amount of lipase, the reactivity can be enhanced by increasing the amount of Mgo.

TABLE 10

|  | QLM (units/g) | | | | |
| --- | --- | --- | --- | --- | --- |
|  | 10 | 25 | 30 | 50 | 50 |
| MgO (%) | 2.5 | 2.5 | 1 | 0.25 | 2.5 |
| EPA area % | 32.1 | 37.17 | 48.2 | 47.8 | 63.9 |
| DHA area % | 13.1 | 15.4 | 17.2 | 17.2 | 17.2 |
| EPA yield (%) | 98.99 | 99.2 | 98.4 | 98.5 | 96.5 |

Example 11

Study of Reaction Time

Lipase QLM (1.65 mg, 100 units/g), water (17 μL), MgO (0.25% (w/w) relative to oil), and of ethanol (one equivalent relative to fatty acids) were added to purified sardine oil (1 g, 28.2% of EPA, 12.5% of DHA, Nippon Suisan Kaisha, Ltd.), and alcoholysis was carried out by stirring for 0 to 24 hours at 40° C.

The results are shown in Table 11.

TABLE 11

|  | Reaction time | | | | | | | |
| --- | --- | --- | --- | --- | --- | --- | --- | --- |
|  | 0 | 1 | 2 | 4 | 6 | 7 | 16 | 24 |
| EPA area % | 28.8 | 39.6 | 42.7 | 44.0 | 44.5 | 46.8 | 50.6 | 53.4 |
| DHA area % | 12.0 | 15.8 | 15.6 | 16.4 | 15.7 | 17.0 | 16.3 | 16.0 |

[Reference Example]
Lipase Reaction without Adding MgO or Water

Lipase QLM (100 to 1,000 units/g) and ethanol (one equivalent relative to fatty acids) were added to purified sardine oil (1 g, 28.2% of EPA, 12.5% of DHA, Nippon Suisan Kaisha, Ltd.), and alcoholysis was carried out by stirring for 16 hours at 40° C.

The results are shown in Table 12. In the reaction system without adding water or MgO, EPA was not concentrated to the level of the present invention, even using 1000 unit/g of lipase.

TABLE 12

|  | QLM (units/g) | | | | |
| --- | --- | --- | --- | --- | --- |
|  | 100 | 250 | 500 | 750 | 1,000 |
| EPA area % | 36.1 | 41.4 | 45.9 | 46.7 | 46.3 |
| DHA area % | 15.2 | 36.1 | 16.2 | 17.92 | 17.97 |
| EPA yield (%) | 85.1 | 76.1 | 69.1 | 72.2 | 71.6 |

Example 12

Application to Coho Salmon Extracted Oil

Lipozyme TL IM (2.0 mg (0.2%), *Thermomyces lanuginosus*, Novozymes), water (10 μL), MgO (Junsei Chemical Co., Ltd., special grade, purity of 99% or higher; 0.5% (w/w) or 2.5% (w/w) relative to oil), and ethanol (170 μL, 0.75 equivalent relative to fatty acids) were added to coho salmon extracted oil (1 g, 9.8% of EPA, 14.0% of DHA), and the mixture was stirred for 16 hours at 40° C. After the reaction was completed, the solid content was filtered off, the glyceride fraction was separated by preparative TLC, conversion thereof to methyl ester was conducted, and the fatty acid composition was analyzed by gas chromatography. The condition for gas chromatography analysis is indicated as follows:

Capillary Column: DB-WAX (J&W Scientific), Fused Silica Capillary Column, 0.25 mm I.D.×30 m, 0.25 μm film thickness;
Carrier gas: helium;
Detector: 250° C., FID;
Inlet: 250° C., split rate=100:1
Column Temp.: 180° C. to 3° C./min, then to 230° C. (15 min)
Apparatus: Hewlett Packard 6890

Moreover, as comparative examples, ethanolysis reaction was carried out under the conditions indicated above with the exception that no water or MgO was added.

Table 13 shows the results regarding EPA and DHA area % of the glyceride fraction, the EPA and DHA yield, and the glyceride yield. Table 14 shows the results of the comparative examples.

TABLE 13

|  | Starting coho salmon extracted oil | 0.2% Lipozyme TL IM 0.5% MgO + Water | 0.2% Lipozyme TL IM 2.5% MgO + Water |
|---|---|---|---|
| EPA area % | 9.8 | 14.0 | 14.0 |
| DHA area % | 14.0 | 30.7 | 45.3 |
| EPA + DHA area % | 23.8 | 44.7 | 59.3 |
| EPA yield (%) |  | 69.6 | 29.1 |
| DHA yield (%) |  | 10.7 | 66.3 |
| Glyceride yield (%) |  | 48.8 | 20.5 |

TABLE 14

|  | 0.2% Lipozyme TL IM without MgO or water |
|---|---|
| EPA area % | 10.33 |
| DHA area % | 15.15 |
| EPA + DHA area % | 25.48 |
| EPA yield (%) | 98.9 |
| DHA yield (%) | 96.9 |
| Glyceride yield (%) | 95.28 |

Example 13

Application to Walleye Pollack Extracted Oil

Walleye pollack extracted oil (1 g, 12.3% EPA, 7.9% DHA) was used as the starting oil and fat. Lipase QLM (1.65 mg, 100 units/g), water (17 µL), MgO (2.5% (w/w)), and ethanol (170 µL) were added to the oil and fat, and ethanolysis reaction was carried out for 16 hours at 40° C. Moreover, ethanolysis reaction using Lipozyme TL IM (5 mg (0.5%)) with addition of water and MgO as carried out in the same manner. Table 15 shows the results of the area % and yields of EPA and DHA, and glyceride yield. EPA was concentrated when Lipase QLM was used, and DHA was concentrated when Lipozyme TL IM was used. The EPA and DHA were concentrated such that their combined area % was at least twice compared with that of the starting material.

As comparative examples, Table 16 shows the results of ethanolysis reaction under the conditions indicated above, with the exception that no MgO or water was added.

TABLE 15

|  | Starting walleye pollack extracted oil | Lipase QLM 100 units/g 2.5% MgO + Water | 0.5% Lipozyme TL IM 2.5% MgO + Water |
|---|---|---|---|
| EPA area % | 12.3 | 30.9 | 14.0 |
| DHA area % | 7.9 | 12.9 | 38.3 |
| EPA + DHA area % | 20.2 | 43.8 | 49.4 |
| EPA yield (%) |  | 103.7 | 18.3 |
| DHA yield (%) |  | 73.7 | 78.1 |
| Glyceride yield (%) |  | 45.1 | 16.2 |

TABLE 16

|  | Lipase QLM 100 units/g without MgO or water | 0.5% Lipozyme TL IM without MgO or water |
|---|---|---|
| EPA area % | 15.8 | 18.6 |
| DHA area % | 9.9 | 16.0 |
| EPA + DHA area % | 25.7 | 34.5 |
| EPA yield (%) | 101.0 | 64.3 |
| DHA yield (%) | 97.8 | 64.1 |
| Glyceride yield (%) | 78.6 | 79.4 |

Example 14

Application to Sunfish Liver Oil

Sunfish liver oil (1 g, 5.1% of arachidonic acid (AA), 4.2% of EPA, 7.7% of docosapentaenoic acid (DPA), and 10.5% of DHA) was used as the starting oil and fat. Lipase QLM (1.65 mg, 100 units/g), water (17 µL), MgO (2.5% (w/w)) and ethanol (170 µL) were added to the oil and fat, and ethanolysis reaction was carried out for 16 hours at 40° C. Moreover, ethanolysis reaction using Lipozyme TL IM (5 mg (0.5%)) with addition of water and MgO was carried out in the same manner. Table 17 shows the area % and yield of AA, EPA, DPA, and DHA and glyceride yield. When Lipase QLM was used, AA, EPA, DPA and DHA were concentrated, while only DHA was concentrated when Lipozyme TL IM was used.

As comparative examples, ethanolysis reaction was carried out under the condition indicated above, except for no addition of MgO or water. The results are shown in Table 18.

TABLE 17

|  | Starting sunfish liver oil | Lipase QLM 100 units/g 2.5% MgO + Water | 0.5% Lipozyme TL IM 2.5% MgO + Water |
|---|---|---|---|
| AA area % | 5.1 | 12.9 | 2.8 |
| EPA area % | 4.2 | 10.7 | 2.6 |
| DPA area % | 7.7 | 17.9 | 3.6 |
| DHA area % | 10.5 | 17.5 | 59.8 |
| AA + EPA + DPA + DHA area % | 27.6 | 59.0 | 68.8 |
| AA yield (%) |  | 95.7 | 8.6 |
| EPA yield (%) |  | 96.8 | 9.9 |
| DPA yield (%) |  | 98.0 | 7.5 |
| DHA yield (%) |  | 81.1 | 90.5 |
| Glyceride yield (%) |  | 44.8 | 15.9 |

TABLE 18

|  | Lipase QLM 100 units/g without MgO or water | 0.5% Lipozyme TL IM without MgO or water |
|---|---|---|
| AA area % | 6.5 | 5.6 |
| EPA area % | 5.3 | 4.5 |
| DPA area % | 10.4 | 8.7 |
| DHA area % | 13.5 | 12.8 |
| AA + EPA + DPA + DHA area % | 35.7 | 31.7 |
| AA yield (%) | 98.5 | 90.3 |
| EPA yield (%) | 99.1 | 89.2 |
| DPA yield (%) | 104.9 | 93.1 |
| DHA yield (%) | 100.1 | 100.0 |
| Glyceride yield (%) | 67.9 | 82.3 |

Example 15

Combination of Two Lipases

Sardine oil (1 g, 15.7% of EPA, 9.0% of DHA, Nippon Suisan Kaisha, Ltd.) was used as starting oil and fat. Combination of Lipase QLM (1.65 mg, 100 units/g) and Lipozyme TL IM (5 mg, 0.5%), water (10 μL), MgO (2.5% or 0.25% (W/W)), and ethanol (170 μL) were added to the oil and fat, and the ethanolysis reaction was carried out for 16 hours at 40° C. Table 19 shows the results of area % and yield of EPA and DHA, and glyceride yield. The results indicate that the combination of Lipase QLM, which has an EPA concentrating effect, and Lipozyme TL LM, which has a DHA concentrating effect, resulted in concentration of both EPA and DHA.

As comparative examples, ethanolysis reaction was carried out in the condition indicated above, except for no addition of MgO or water. The results are shown in Table 20.

TABLE 19

|  | Starting sardine oil | Lipase QLM 100 units/g + 0.5% Lipozyme TL IM 2.5% MgO + water | Lipase QLM 100 units/g + 0.5% Lipozyme TL IM 0.25% MgO + water |
|---|---|---|---|
| EPA area % | 15.7 | 30.8 | 25.8 |
| DHA area % | 9.0 | 31.8 | 19.6 |
| EPA + DHA area % | 24.7 | 62.6 | 45.4 |
| EPA yield (%) |  | 48.9 | 60.2 |
| DHA yield (%) |  | 88.2 | 80.0 |
| Glyceride yield (%) |  | 21.4 | 32.2 |

TABLE 20

|  | Lipase QLM 100 units/g + 0.5% Lipozyme TL IM without MgO or water |
|---|---|
| EPA area % | 22.1 |
| DHA area % | 14.0 |
| EPA + DHA area % | 36.1 |
| EPA yield (%) | 101.4 |
| DHA yield (%) | 102.5 |
| Glyceride yield (%) | 72.1 |

INDUSTRIAL APPLICABILITY

The present invention can provide oil and fat containing PUFAs such as EPA, DHA and the like in high concentration. As a result, a smaller amount of oil and fat than ever before is required to add a certain amount of PUFAs such as EPA, DHA and the like to health food products.

The invention claimed is:

1. A process for preparing concentrated polyunsaturated fatty acid oil, which comprises:
    subjecting oil and fat that contain polyunsaturated fatty acid as a fatty acid composing the oil and fat to an alcoholysis reaction using lipase in the presence of alcohol, added water and at least one compound, as a reaction additive, selected from magnesium oxide, magnesium hydroxide, calcium oxide and calcium hydroxide; and
    separating a glyceride fraction that contains concentrated polyunsaturated fatty acid,
    wherein the amount of the reaction additive is 0.05% to 5% (w/w) relative to the oil and fat containing polyunsaturated fatty acid, and the amount of the added water is 5% to 20% (v/v) relative to the alcohol,
    wherein the polyunsaturated fatty acid is eicosapentaenoic acid, docosahexaenoic acid, arachidonic acid, or a combination thereof, and
    wherein the lipase is selected from the lipases obtained from the microorganisms of *Alcaligenes* sp., *Thermomyces lanuginosus, Burkholderia cepacia*, and *Pseudomonas fluorescens*.

2. The process according to claim 1, wherein the reaction additive is magnesium oxide.

3. The process according to claim 2, wherein the alcoholysis reaction is ethanolysis.

4. The process according to claim 3, wherein the polyunsaturated fatty acid is eicosapentaenoic acid, docosahexaenoic acid, or a combination thereof.

5. The process according to claim 4, wherein the oil and fat containing polyunsaturated fatty acid is fish oil.

6. The process according to claim 1, wherein the alcoholysis reaction is ethanolysis.

7. The process according to claim 6, wherein the polyunsaturated fatty acid is eicosapentaenoic acid, docosahexaenoic acid, or a combination thereof.

8. The process according to claim 6, wherein the oil and fat containing polyunsaturated fatty acid is fish oil.

9. The process according to claim 1, wherein the polyunsaturated fatty acid is eicosapentaenoic acid, docosahexaenoic acid, or a combination thereof.

10. The process according to claim 1, wherein the oil and fat containing polyunsaturated fatty acid is fish oil.

* * * * *